(12) United States Patent
Mullaly et al.

(10) Patent No.: US 7,704,076 B2
(45) Date of Patent: Apr. 27, 2010

(54) DENTAL ATTACHMENT ASSEMBLY AND METHOD

(75) Inventors: Scott Mullaly, San Marcos, CA (US); Paul Zuest, Valley Center, CA (US)

(73) Assignee: Zest IP Holdings LLC, Escondido, CA (US)

( * ) Notice: Subject to any disclaimer, the term of this patent is extended or adjusted under 35 U.S.C. 154(b) by 103 days.

(21) Appl. No.: 11/613,464

(22) Filed: Dec. 20, 2006

(65) Prior Publication Data

US 2008/0153063 A1    Jun. 26, 2008

(51) Int. Cl.
*A61C 8/00* (2006.01)
(52) U.S. Cl. .................................. 433/174; 433/172
(58) Field of Classification Search ......... 433/172–176, 433/220, 221, 215; 623/16.11, 17.17
See application file for complete search history.

(56) References Cited

U.S. PATENT DOCUMENTS

| | | | |
|---|---|---|---|
| 3,514,858 A | 6/1970 | Silverman | |
| 4,290,755 A | 9/1981 | Scott | |
| 4,488,874 A | 12/1984 | Soifer | |
| 4,540,367 A | 9/1985 | Sule | |
| 4,547,156 A | 10/1985 | Hader | |
| 4,993,950 A | 2/1991 | Mensor | |
| 5,049,072 A * | 9/1991 | Lueschen | 433/173 |
| 5,120,222 A | 6/1992 | Sule | |
| 5,195,891 A | 3/1993 | Sule | |
| 5,211,561 A | 5/1993 | Graub | |
| 5,234,341 A | 8/1993 | Johansen | |
| 5,246,368 A | 9/1993 | Sillard | |
| 5,413,480 A | 5/1995 | Musikant et al. | |
| 5,417,570 A | 5/1995 | Zuest et al. | |
| 5,480,304 A | 1/1996 | Nardi | |
| 5,520,540 A | 5/1996 | Nardi et al. | |
| 5,556,280 A | 9/1996 | Pelak | |
| 5,630,717 A | 5/1997 | Zuest et al. | |
| 5,749,732 A | 5/1998 | Sendax | |
| 5,997,300 A * | 12/1999 | Tseng | 433/177 |
| 6,030,219 A | 2/2000 | Zuest et al. | |

(Continued)

FOREIGN PATENT DOCUMENTS

EP    0 037 864 A1    10/1981

(Continued)

OTHER PUBLICATIONS

Locking Overdenture Attachments, to the Point Attachments International, Inc. Newsletter, vol. 13, Summer 1994, pp. 1-3.

(Continued)

*Primary Examiner*—Ralph A Lewis
*Assistant Examiner*—Yogesh Patel
(74) *Attorney, Agent, or Firm*—Mayer Brown LLP (57) ABSTRACT

A dental attachment system has an abutment member configured for attachment to a tooth root, implant, or adjacent tooth, the abutment member having a head and an annular seat adjacent the head. An elastomeric ring is configured for releasable engagement in the seat on the abutment member, and is retained in a retainer ring which in turn is in swivel engagement with a concave inner surface of a cavity in a cap which is secured in a recess in a dental appliance such as a denture, partial denture, or the like.

25 Claims, 6 Drawing Sheets

U.S. PATENT DOCUMENTS

| | | | |
|---|---|---|---|
| 6,299,447 B1* | 10/2001 | Zuest et al. | 433/172 |
| 6,302,693 B1* | 10/2001 | Mena | 433/172 |
| 6,716,030 B1* | 4/2004 | Bulard et al. | 433/174 |
| 6,981,871 B2 | 1/2006 | Mullaly et al. | |
| 2004/0005530 A1* | 1/2004 | Mullaly et al. | 433/172 |
| 2006/0269903 A1* | 11/2006 | Bulard et al. | 433/174 |

OTHER PUBLICATIONS

Stud Attachments Comparison, Swiss NF Metals, Inc., Attachments International, Inc. 1999.

Stud Type Overdentures- An Overview, to the Point Attachments International, Inc. Newsletter, vol. 20, Spring 1999, pp. 1-3.

Rhein 83 Castable Spherical Attachment, Advertisement, Dental Products.net, Date Unknown.

Rhein 83 Sphero- Overdentures Self-Parallel Attachment, Advertisement, Date Unknown.

VKS-OC RS Matrix System Advertisement, Bredent USA, Date Unknown.

Bredent VKS-OC RC Attachment Systems, Advertisement from Canadian Journal of Dental Technology, Date Unknown.

Lindberg Homburger Modent Dental, Product Showcase, p. 80, The Canadian Journal of Dental Technology, Fall 2000.

Steri-OSS Replace Overdenture Stud Type Attachments Order Sheet, Date Unknown.

OCO Biomedical Corporate Profile, Dental Products Report, Aug. 2005, pp. 131 and 133.

OCO Inc. Dental Implant Brochure, Feb. 2005.

Imtec Mini Dental Implant Brochure, 2003, Front page & pp. 2-7, 11, 18-20.

International Search Report/Written Opinion issued in PCT/US07/87284 on Jun. 26, 2008.

* cited by examiner

DENTAL ATTACHMENT ASSEMBLY AND METHOD

BACKGROUND

1. Field of the Invention

The present invention generally relates to a dental attachment or anchoring structure for attaching a removable dental appliance such as a full denture, overdenture, partial denture, or the like to a remaining non-vital root, an adjacent tooth, or to an endosseous implant.

2. Related Art

There are many different types of dental attachments for releasably anchoring a dental appliance to one or more roots or implants, or to an adjacent tooth. In many cases, the attachments comprise mating, snap engageable male and female parts, one of which is attached to the denture and the other of which is attached to a root, implant, or adjacent tooth. One known attachment has a first part which is pivotally engaged in a cap secured in an implant, and a second part secured to an implant, root, or the like. Some attachments of this general type are described in U.S. Pat. Nos. 5,417,570, 6,030,219, and 6,299,447, for example.

Another known attachment uses an O-ring which engages over a ball at the end of an implant abutment or post. In one example, the O-ring engages in a retainer which is attached to a denture. One problem with O-ring or similar resilient ring attachments is that they work best when perfectly straight. Any angulation of the abutment will cause wear and roll-out of the ring due to uneven biting forces.

SUMMARY

The present invention provides a system and method for attaching a dental prosthesis to a tooth root, implant, or adjacent tooth. In one embodiment, an attachment system comprises an abutment member for attachment to a tooth root, implant, or adjacent tooth, an elastomeric ring for engagement in a groove on the abutment member, a retainer ring for engagement over the elastomeric ring, the retainer ring having a rounded outer surface, and a cap for securing in a recess in a dental appliance or prosthesis, the cap having a rounded, concave inner surface adapted for swivel engagement over the rounded outer surface of the retainer ring.

This arrangement provides vertical resilience due to the elastomeric ring as well as a pivoting action which can compensate for divergent implants. The abutment member may have a tail end portion configured for engagement in a mating bore in a non-vital root or an implant bonded into a root, or may have a distal extension for securing to an adjacent tooth, crown, or the end of a bar. In another embodiment, one or more abutment members are cast onto an elongate bar secured to two or more implants. The cap, retainer ring, and elastomeric ring may be adapted for use separately with an existing abutment for any O-ring attachment, allowing such existing abutments to be retrofitted with a pivoting or swiveling cap attachment.

In one embodiment, the abutment member may be a mini or small diameter implant with a threaded shaft or tail portion which is adapted to be implanted directly into a prepared bore in a patient's jaw bone. A series of such small abutment members may be splinted together by means of a bar of relatively small cross-sectional dimensions for added stability.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for systems and methods for removably attaching a dental appliance such as a full denture, overdenture, partial denture, or the like in the mouth of a patient. For example, one method as disclosed herein allows for a cap to be cemented to the appliance with a resilient ring and outer, ring-shaped retainer pivotally mounted in the cap and adapted for snap engagement over the head of an abutment secured at an appropriate location in a patient's mouth.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figures 1, 2, 3, 4, 5:
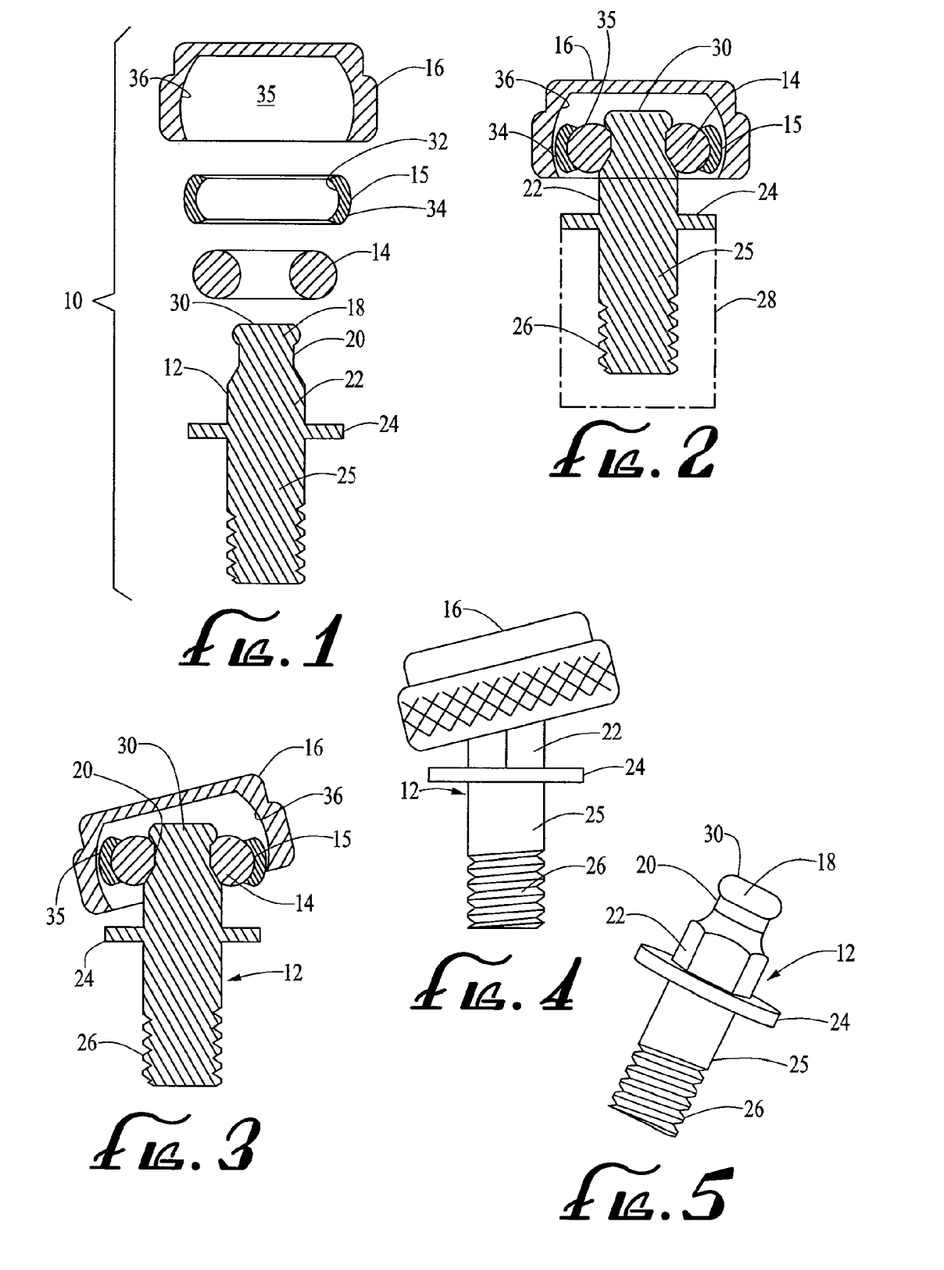
FIG. 1 is a sectional view of a dental attachment assembly according to a first embodiment, with the parts of the assembly separated.
FIG. 2 is a sectional view of the dental attachment assembly of FIG. 1, with the parts assembled together.
FIG. 3 is a sectional view similar to FIG. 2, illustrating the pivoting action of the cap.
FIG. 4 is a side elevation view of the assembled dental attachment assembly of FIGS. 1 to 3, with the cap pivoted out of alignment with the remainder of the assembly.
FIG. 5 is a side elevation view of the abutment member of the attachment assembly of FIGS. 1 to 4.

FIGS. 1 to 5 illustrate a dental attachment assembly 10 according to a first embodiment. As best illustrated in FIG. 1, the assembly 10 comprises four parts, specifically an abutment member 12 for attachment to a non-vital root, implant, or the like, an elastomeric ring 14 which may be an O-ring or the like, an outer retainer ring 15 for elastomeric ring 14, and a cap 16 for securing in an indent in a denture or partial denture. One or more such assemblies may be secured in a denture, depending on the extent of the denture.

The abutment member 12 is shown separately in FIG. 5 and has a head 18, an annular seat or groove 20 adjacent head 18, a hexagonal portion 22, annular flange 24 adjacent the hexagonal portion, and a tail or shaft 25 extending from flange 24 away from the head of the member 12. The abutment member is of a suitable strong material such as titanium, titanium alloy, or stainless steel with a titanium nitride coating. The shaft 25 has a threaded end portion 26 for attachment in a prepared bore in a tooth root or in the bore of an implant 28, as indicated in dotted outline in FIG. 2. The head 18 has a rounded or convex outer annular surface and a flattened end face 30. As illustrated in FIG. 1, the flattened end face has a diameter larger than the height of the head. The hexagonal portion has flat faces for engagement by a suitable tool for use in screwing the member 12 into a tooth root or implant bore. In alternative embodiments, other non-circular or polygonal shapes with flats for engagement by a suitable tool may be used for tool-engaging portion 23, such as square, octagonal, or the like.

The elastomeric ring 14 may be an O-ring or similar annular member of elastomeric material. Examples of suitable materials for ring 14 are natural or synthetic rubber material such as Buna or silicone rubber of 70 to 90 Durometer. The O-ring may be of any desired hardness or durometer. Ring 14 is adapted for engagement in annular seat or groove 20 when stretched over head 30, as illustrated in FIGS. 2 and 3. The retainer ring 15 which holds the O-ring is an annular member of more rigid material than the O-ring, such as stainless steel or titanium, or a rigid plastic material such as Delrin®, manufactured by E.I. du Pont de Nemours and Company, or the like. The retainer ring 15 has a rounded, concave inner surface 32 of suitable dimensions for retaining elastomeric ring 14, and a generally convex, rounded outer surface 34.

The cap 16 is of a rigid material such as stainless steel, titanium or the like, and has an open end and inner cavity 35 for receiving the retainer ring 15 and elastomeric ring 14. Cavity 35 has a generally concave, rounded inner annular surface 36 for pivoting or swivel engagement over the rounded outer surface 34 of retainer ring 15, as illustrated in FIGS. 2 and 3, and a flat inner end face which faces the end face 30 of the head 18. As illustrated in FIG. 2, there is a significant gap or clearance between the inner end face of cap 16 and the end face 30 of head 18, which allows the cap to swivel through a relatively large angle relative to the abutment member, as seen in FIG. 3, compensating for off-angle or non-parallel abutments. As illustrated in FIGS. 1 to 3, the height of retainer ring 15 is significantly less than the height of cavity 35, and there is also a clearance between the retainer ring 15 and the flat inner end face of the cavity in the straight, assembled condition of FIG. 2, which also allows for the swiveling movement of the cap relative to the assembled retainer ring 15, O-ring 14, and head 30, as seen in FIG. 3. The outer surface of cap 16 may be knurled or roughened as indicated in FIG. 4 for better retention in the denture recess.

In operation, the abutment member 12 is installed in a suitable bore in an implant or root. One or more abutment members may be installed at suitable locations in a patient's mouth, with corresponding caps 16 located in the denture. The retainer ring and enclosed O-ring 14 are held in the cap and can be snapped over the head of an aligned abutment member in order to install the denture. FIGS. 2 and 3 illustrate the attachment assembly in the installed condition. The resilient ring 14 provides vertical movement while the cap pivots over the ring 15 as indicated in FIGS. 3 and 4, to compensate for any off-angle abutments. This arrangement therefore allows for a significant amount of movement and can dissipate some stress away from the implant and abutment. The pivoting cap allows pivoting motion without flexing the O-ring 14. The flattened end 30 of the abutment member allows the denture to sit lower over the abutment than with an abutment with a spherical or ball-shaped head. As can be seen in FIGS. 1 and 2, the height of the head 18 is less than the diameter of O-ring 14 and is also less than the height of retainer ring 15, and the head protrudes only a small distance above the top of the O-ring and retainer ring in the installed condition of FIG. 2.

The attachment assembly can be made in a range of different sizes for different size patients and dental implants. In one embodiment the heads of the abutment members are provided within a range of diameters from 1.8 mm. to 6.0 mm., and the length is in the range from 7 mm. to 18 mm. The diameter of the seat 20 is in the range from 1.0 mm to 3.0 mm, while the 0-ring 14 is of suitable dimensions for mating snap engagement in seat 20. The cap, resilient ring and retainer may be sold separately for fitting over any O-ring ball abutment.

Figures 6, 7, 8, 9, 10, 11:
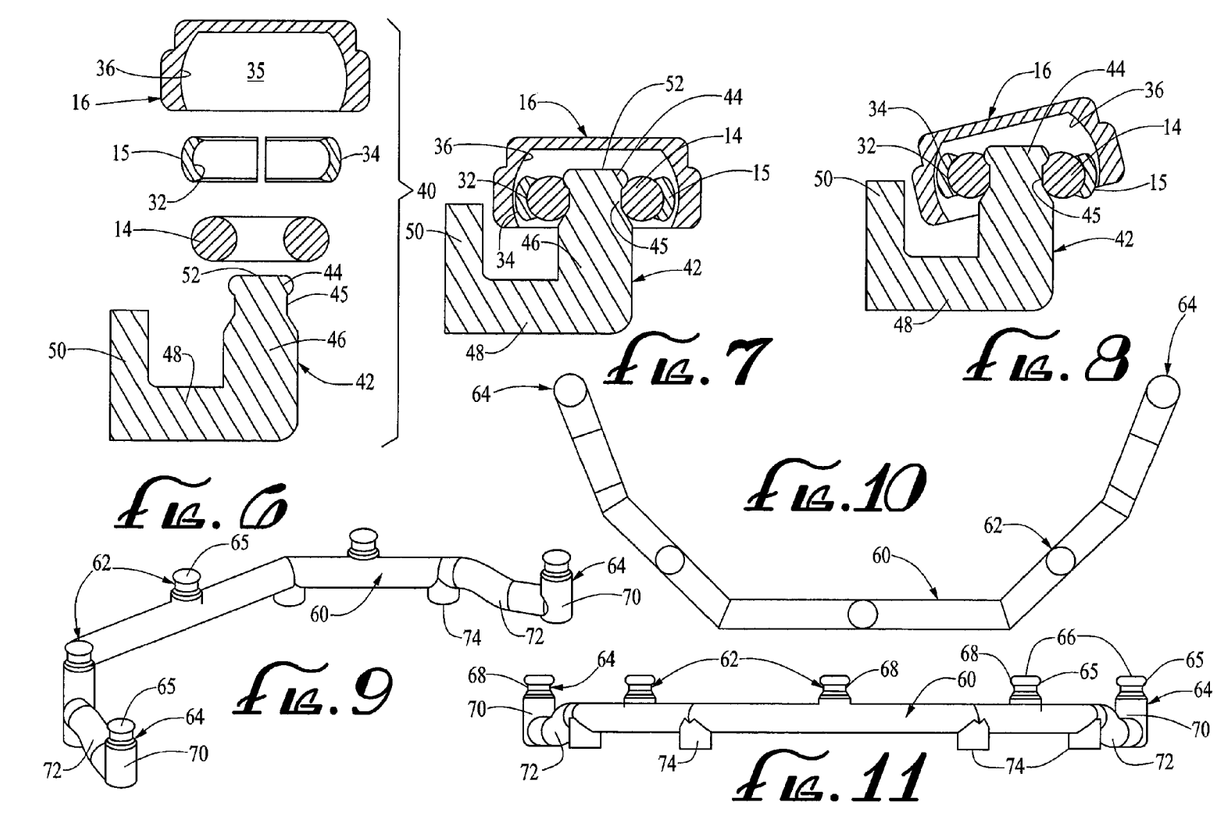
FIG. 6 is a sectional view of a distal extension dental attachment assembly of another embodiment designed for attachment to an adjacent tooth or crown, with the parts separated.
FIG. 7 is a sectional view of the dental attachment assembly of FIG. 6, with the parts assembled.
FIG. 8 is a sectional view similar to FIG. 7, illustrating the pivoting action of the cap.
FIG. 9 is a perspective view of a dental attachment bar of another embodiment.
FIG. 10 is a top plan view of the bar of FIG. 9.
FIG. 11 is a front elevation view of the bar of FIGS. 9 and 10.

FIGS. 6 to 8 illustrate a modified abutment assembly 40 which is designed for attachment to an adjacent tooth or crown rather than to a root or implant. The assembly is similar to that of the previous embodiment apart from the abutment member 42, and like reference numerals have been used for like parts. Abutment member 42 has a head 44, an annular seat or groove 45 adjacent the head 44, a shaft portion 46 aligned with the head and groove, and a distal extension or connecting arm 48 extending radially from shaft portion 46 and terminating in a plate portion 50 which is secured in a suitable slot provided in the side of an adjacent tooth or crown. As in the previous embodiment, the head 44 has a flattened end 52 for reduced height.

As in the previous embodiment, a resilient ring 14 is adapted for snap engagement over head 44 and into groove 45, as illustrated in FIGS. 7 and 8, and a retainer ring 15 engages over ring 14. Retainer ring 15 and resilient ring 14 are pivotally engaged the cavity 35 in cap 16. As in the previous embodiment, the retainer and resilient rings are held in axial alignment with head 44 of abutment member 42 while the cap 16 can pivot or swivel on retainer ring 15 as indicated in FIG. 8 in order to adjust for divergent tooth roots or implant placements.

FIGS. 7 and 8 illustrate the implant assembly in an installed or assembled condition. The cap containing the retainer ring 15 and O-ring or elastomeric ring 14 is suitably processed (bonded) in a recess in a denture. The denture is then pushed into position, with the O-ring 14 stretching over head 44 and then snapping into groove 45, where it is releasably retained. At the same time, the cap 16 can swivel to accommodate non-straight implants or tooth roots without flexing the O-ring, as indicated in FIG. 8. The dimensions of the components in this embodiment are similar to the previous embodiment.

FIGS. 9 to 11 illustrate an implant retained, cast bar 60 forming part of a denture attachment assembly according to another embodiment. Bar 60 has multiple abutment members 62 cast at spaced locations along the bar. Additionally, distal extension abutment members 64 are secured at each end of the bar 60. Each abutment member 62, 64 has a shape identical or similar to the head and annular seat or groove portion of the abutment members in the previous embodiments.

Each cast abutment member 62 along the length of the bar has a head 65 of equivalent shape to head 18 and 44 of the previous embodiments, with a flattened end 66, and an annular seat or groove 68 adjacent the head 65, and joins to the bar adjacent groove 68. The end or distal extension abutment members also each have a head 65 with a flattened end 66 and a groove 68 adjacent the head, and a post 70 extending from groove 68 and integrally cast with bar 60 via a distal extension 72 from post 70. The distal extensions 72 are selected with an appropriate drop down dependent on the gum and jaw recession at the respective locations in the patient's jaw.

The bar has fastener devices at spaced intervals for securing the bar to spaced implants or tooth roots, in the manner described in U.S. Pat. No. 5,630,717 of Zuest et al., the contents of which are incorporated herein by reference. Fastener screw devices (not illustrated) may be secured in sockets 74 on the opposite face of bar 60 to abutment members 62 for attachment purposes.

The abutment members 62, 64 on the bar 60 are adapted for releasable snap engagement with elastomeric ring 14 of the previous embodiments exactly as described above in connection with those embodiments, and the head and seat may be of similar dimensions to the previous embodiments. An overdenture for attachment to bar 60 is provided with appropriately positioned caps 16 each containing a swiveling retainer ring 15 and enclosed elastomeric ring 14 for snap engagement over the respective heads 65.

Figures 12, 12A, 13, 14, 15:
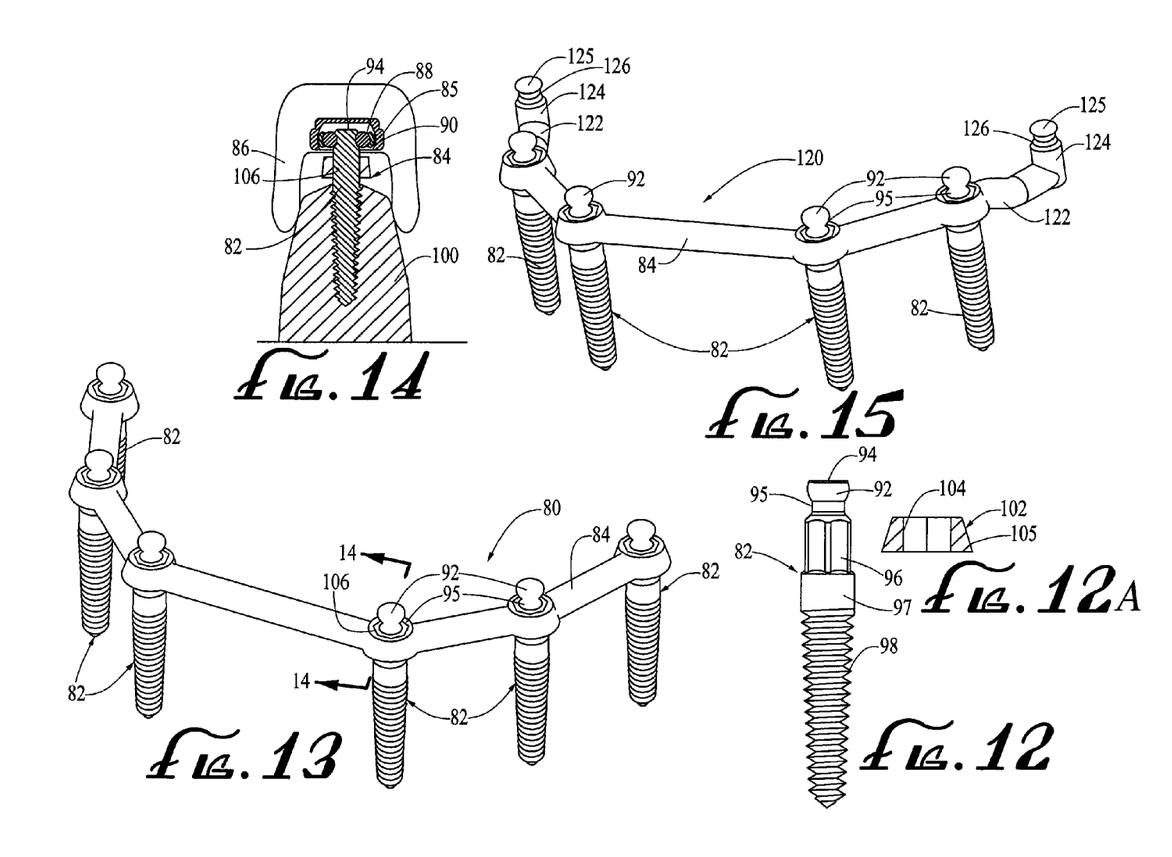
FIG. 12 is a side elevation view of a mini dental implant and separated collar or coping according to another embodiment.
FIG. 13 is a perspective view illustrating splinting of several of the implants of FIG. 12 with a bar.
FIG. 14 is a cross-sectional view on the lines 14-14 of FIG. 13.
FIG. 15 is a perspective view similar to FIG. 13 illustrating an alternative bar configuration.

FIGS. 12 to 14 illustrate an attachment assembly 80 according to another embodiment of the invention. In this embodiment, the attachment assembly comprises a plurality of mini or small diameter implants 82 splinted together by a bar 84. A cap 85 is appropriately positioned in an overdenture 86 for alignment with each implant, as illustrated in FIG. 14, and each cap contains a swiveling retainer ring 90 with an elastomeric ring 88 retained within ring 86 of suitable dimensions for snap engagement over the head of a mini implant 82. The retainer ring 90, elastomeric ring 88 and cap 85 are identical in shape and operation to the corresponding components of the previous embodiments, but of smaller dimensions to correspond to the small dimensions of the mini implants 82.

A mini abutment member or implant 82 is illustrated in more detail in FIG. 12, and has a head 92 with a flattened end 94, an annular seat or groove 95 for receiving elastomeric ring 88 adjacent the head 90, a tool engaging portion 96 which may be of hexagonal or other polygonal cross-sectional shapes, a smooth annular interface portion 97, and a tapered, threaded shaft 98 extending from portion 97 to the end of implant 82. The implant 82 is of a suitable strong material, typically a metal such as titanium or an alloy of titanium with another metal, or stainless steel with a titanium nitride coating. The threaded shaft 98 is designed for threaded engagement in a prepared bore in endosseous bone 100, as indicated in FIG. 14. The head diameters of the implant in one embodiment are in the range from around 1.5 mm to 4.0 mm, while the diameter of seat 95 is from 1.0 mm to 3.0 mm, and the implant length is in the range from around 7.0 mm. to 22.0 mm.

As illustrated in FIG. 12A, a coping or collar 102 having a hex bore 104 and a tapered outer surface 105 is designed for loose fitting over the hexagonal portion 96 of the implant 82 so as to allow casting of bar 84. In order to make the bar 84, the desired number of implants 82 are first appropriately secured at the desired locations in the patient's jaw. An impression is then taken of the implant locations in the jaw, and this impression is used in the dental laboratory to fabricate a model of the patient's jaw, including implant analogs at the implant locations with the corresponding relative orientations. A coping or collar 102 is then engaged over each implant analog, and a wax bar section is secured between each adjacent pair of collars 102. The resultant castable framework is fitted in the patient's jaw and re-shaped as necessary for the proper fit. Finally, the fitted plastic or wax bar framework is used to cast a matching metal bar which has hex bores 106 at the appropriate positions and orientations for engagement over the hex portions 97 of the implants. The bar is then engaged over all the implants in the patient's jaw and cemented in place.

This arrangement provides a splint between the implants, which may help distribute load. As illustrated in FIG. 14, the denture 86 floats on the tissue when installed over the heads 92 of the implants 82 connected by bar 84, rather than on the bar as in previous bar supported arrangements. In the illustrated embodiment, the denture does not contact the bar. Instead, it is supported on the O-ring attachments which are spaced above the bar. The bar is used for splinting purposes only in this embodiment.

The flat top 94 of the head of the implant in FIGS. 12 to 14 conserves space and reduces the height of the implant above the gum or tissue. The bar dimensions may be relatively small, and the bar may be of the order of 2.0 mm. in thickness in some embodiments.

FIG. 15 illustrates a modified bar attachment assembly 120 which is similar to the arrangement of FIGS. 12 to 14, and like reference numbers are used for like parts as appropriate. The modification in this embodiment is the addition of a distal extension 122 at each end of the bar 84, along with an integral post 124 at the outer end of each extension. Each post 124 has an enlarged head 125 identical to head 92 at the top of each implant 82, and an annular seat or groove 126 between head 125 and post 124 for receiving an O-ring 88 in a retainer ring 90, as shown in FIG. 14 for the head of one of the implants. This provides attachment points for installation of a denture over regions of the jaw when there is insufficient space or bone depth to introduce implants.

FIGS. 16 to 20 illustrate a dental attachment assembly 150 which is a modification of the first embodiment of FIGS. 1 to 6, and like reference numbers are used for like parts as appropriate. The assembly comprises an abutment member 152 which is similar to the abutment member 12 of FIGS. 1 to 4 apart from the shorter hexagonal portion 154, an elastomeric ring 14, an outer retainer ring 155 for holding the elastomeric ring or O-ring 14, and a cap 156 for securing in an indent in a denture or partial denture. The materials of the components of assembly 150 may be the same or similar to the materials described above in connection with the first embodiment.

Figures 16, 17, 19, 21:
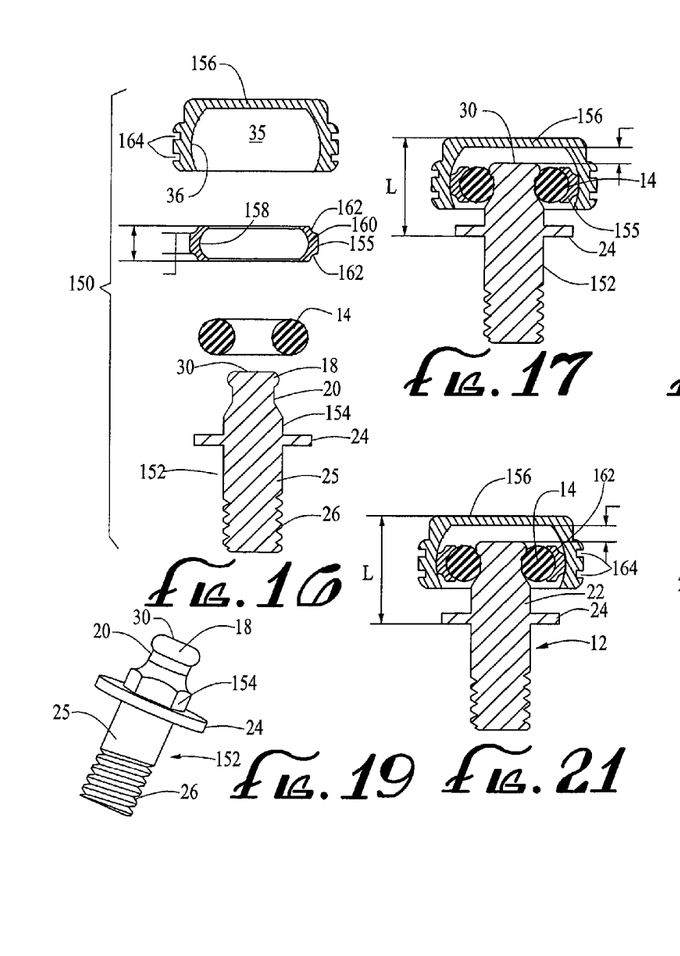
FIG. 16 is an exploded sectional view of a modified embodiment of the dental attachment assembly of FIGS. 1 to 5, with the parts of the assembly separated.
FIG. 17 is a sectional view of the dental attachment assembly of FIG. 16, with the parts assembled together.
FIG. 19 is a side elevation view of the abutment member of the attachment assembly of FIGS. 16 to 18.
FIG. 21 is a sectional view similar to FIG. 17, illustrating a modified abutment member.

The abutment member 152 is shown separately in FIG. 19 and has a head 18, annular seat or groove 20 adjacent head 18, a tool-engaging portion 154 which may be of hexagonal or other polygonal shapes, flange 24, and shaft 25 which has a threaded end portion 26. As noted above, tool-engaging portion 154 of member 152 is shorter than the hexagonal or tool-engaging portion 22 of the abutment member of FIGS. 1 to 6, so that the overall height of the assembly is reduced.

Figures 18, 20, 22:
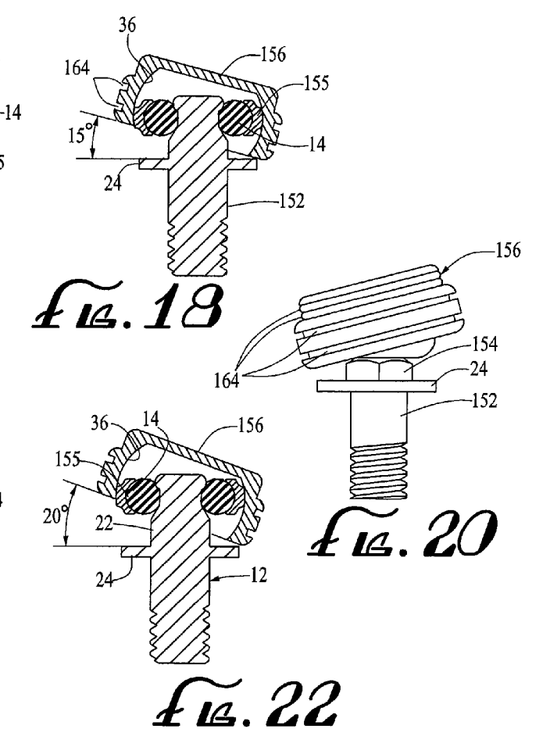
FIG. 18 is a sectional view similar to FIG. 17, illustrating the pivoting action of the cap.
FIG. 20 is a side elevation view of the assembled dental attachment assembly of FIGS. 16 to 19, with the cap pivoted out of alignment with the remainder of the assembly.
FIG. 22 is a sectional view of the assembly of FIG. 21 illustrating the range of pivoting action.

The retainer ring 155 has a rounded inner surface 158 for engaging over the outer surface of O-ring 14 so as to hold the ring. The outer surface of the retainer ring in this embodiment is modified. Instead of having a continuous outer rounded surface, as in the previous embodiments, retainer ring 155 in this embodiment has a central arcuate or rounded portion 160 with upper and lower notches or indents 162. The overall height of the retainer ring 155 is of the order of 0.050 inches while the height of the central, rounded portion is around 0.030 inches.

The cap 156 is also modified in this embodiment. Instead of having an outer, knurled surface as in the previous embodiments, the cap has grooves 164 on its outer surface. The inner cavity 35 is similar or identical to the cap cavity in the previous embodiments, and like reference numerals are used as appropriate.

Operation of the attachment assembly of FIGS. 16 to 20 is similar to that of FIGS. 1 to 6. The threaded portion 26 of abutment member 152 is engaged in a tooth root or implant, while cap 156 containing the retainer ring 155 and O-ring 14 is bonded in an indent in a denture or other dental appliance. The O-ring can then be snapped over the head 18 of abutment member 152 and into seat 20, as illustrated in FIGS. 17 and 18. Once installed, the cap can pivot relative to the retainer ring as indicated in FIG. 18. The notch at the upper end of the retainer ring allows the cap to pivot through a larger angle before contacting the upper edge of ring 156, as can be seen by comparing FIGS. 3 and 18. In the illustrated embodiment, the maximum pivot angle is of the order of 15 degrees.

FIGS. 21 and 22 illustrate a modification in which the abutment member 152 of FIGS. 16 to 18 is replaced by the abutment member 12 of FIG. 1, which has a longer tool-engaging portion 22. All other parts are the same as in FIGS. 16 to 20 and like reference numerals have been used as appropriate. By providing a larger spacing between the retainer ring 155 and the flange 24, the cap can pivot through a larger angle than in the previous embodiment, as can be seen by comparison of FIGS. 18 and 22. When the cap is aligned with the abutment member as in FIGS. 17 and 21, the spacing L between the lower face of the flange 24 and the upper face of the cap 156 is around 0.141 inches (3.6 mm) in FIG. 17 and 0.154 inches (3.9 mm) in FIG. 21. This enables the cap to pivot through around 20 degrees before hitting flange 24 when the longer abutment is used, as illustrated in FIG. 22.

The modified retainer ring and cap of FIGS. 16 to 22 may also be used in place of the retainer ring 15 and cap 16 as used in any of the alternative embodiments of FIGS. 6 to 15.

Figure 23:
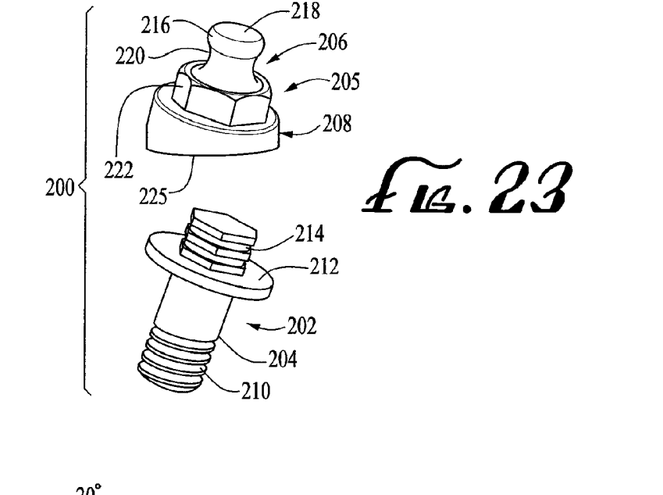
FIG. 23 is a separated perspective view of two parts of an angle correction abutment member for an O-ring attachment assembly according to another embodiment.
Figure 24:
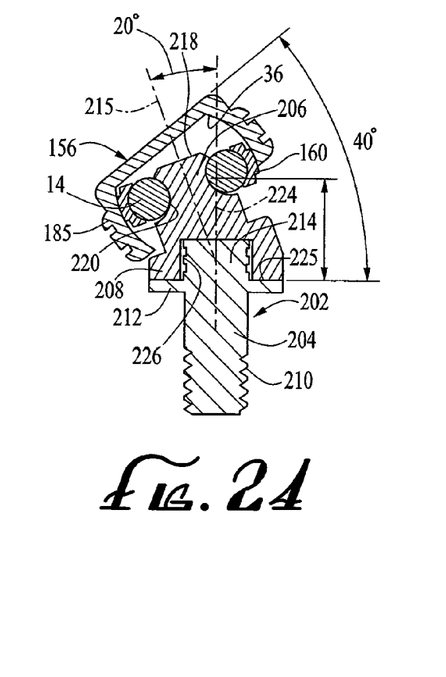
FIG. 24 is a sectional view of an assembled O-ring attachment assembly using the angle correction abutment member of FIG. 23.

FIGS. 23 and 24 illustrate a modified attachment assembly for use when a larger amount of angle correction is necessary due to more divergent implants. The pivoting cap 156, retainer ring 155, and O-ring 14 in this embodiment are identical to that of FIGS. 16 to 22, as illustrated in FIG. 24, and like reference numbers are used for like parts as appropriate. However, in this embodiment, the one-piece, axially aligned abutment member 152 of FIGS. 16 to 22 is replaced by a two part abutment device 200 having a first part 202 with a threaded shaft 204 for engagement in a divergent tooth root or implant, and a second, angle adjusting part 205 having a first, head portion 206 and a second, angled portion 208 extending at a predetermined angle to the head portion 206.

Shaft 204 of the first part 202 has a threaded end portion 210, an annular flange 212, and a mating portion or post 214 projecting upwardly from flange 212 for engagement with the second part 205 of the abutment. In the embodiment illustrated in FIGS. 23 and 24, head portion 206 of the second part has a central axis 215, a head 216 with a flat end 218, an annular groove 220 adjacent the head for receiving an O-ring, and a tool-engaging portion 222 adjacent the groove which may be of hexagonal or other polygonal shapes. The angled portion 208 has an angled, flat end face 225, and a bore 226 in end face 225 designed for engagement with the post 214 of the first abutment part 202. As seen in FIG. 24, bore 226 has a central axis at an angle to head portion axis 215 and perpendicular to end face 225. Thus, when the bore 226 is engaged co-axially over post 214, the head portion 206 will extend at an angle to the axis of shaft 204 to provide a predetermined angle connection and provide at least some degree of compensation for a non-vertical implant placement or root. In the illustrated embodiment, the bore 226 and post 214 are of mating hexagonal shape, but may be of other polygonal shapes in alternative embodiments. In this embodiment, the head portion 206 is at an angle of around 20 degrees the axis 224 of the bore in angled portion 208, but head portions may be provided at different angles in other embodiments, such as 10 degrees as illustrated in FIG. 25.

In this embodiment, the part 202 is first secured in a divergent tooth root or implant using threaded end portion 210. A suitable hex tool can engage post 214 in order to install the first part 202 of the abutment. The post 214 will then extend at the same angle as the divergent root or implant along axis 224. A second part 205 at an appropriate angle is then selected, based on the angle of the divergent root or implant. The second part 205 is then engaged over the post 214 such that the head portion axis 215 is substantially vertically oriented in the jaw, in spite of the divergent implant or root angle. The bore 226 is then cemented in place over post 214.

The installed abutment device 200 is designed for releasable mating engagement with the same pivoting O-ring or resilient ring in a cap as in the previous embodiments, as indicated in FIG. 24. The cap 156, retainer ring 155, and O-ring 14 of this embodiment are the same as in FIGS. 16 to 22, but the device may also be used with the cap, retainer ring, and O-ring of any of FIGS. 1 to 15 in alternative O-ring attachment assemblies. The cap 156 containing the pivoting retainer ring 155 and O-ring 14 is first bonded in an indent in a denture or other dental appliance. The O-ring 14 is then snapped over the head 216 of the abutment device and engages in groove 220, as illustrated in FIG. 24. The cap 156 can then pivot relative to the head of the abutment device, to provide more compensation for off-angle implants and any deviation of the head portion 206 from the vertical orientation. The angled abutment device together with the pivoting cap allow the cap to be pivoted up to 40 degrees relative to the central axis 224 of the first part of the abutment device, and thus the axis of the tooth root or implant to which the implant device is secured.

Figure 25:
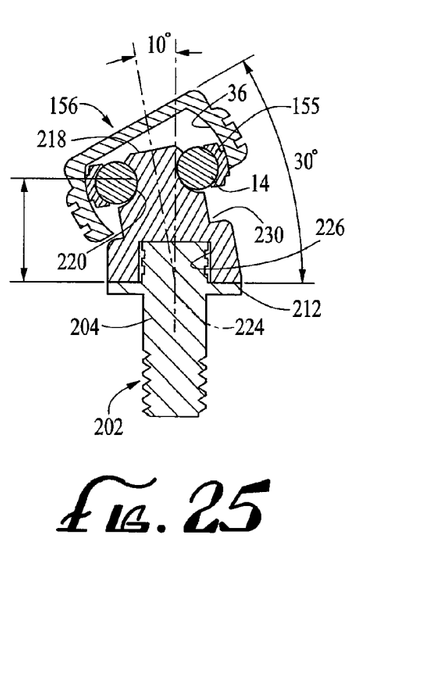
FIG. 25 is a sectional view similar to FIG. 24 illustrating an O-ring attachment assembly with a modified angle correction abutment member for providing a different angular adjustment.

The attachment assembly of FIG. 25 has a similar two part abutment device to the previous embodiment, except for the fact that axis 224 of the bore in the second part 230 of the abutment device is angled at ten degrees relative to the first part, rather than twenty degrees as in the previous embodiment. The assembly of FIG. 25 is otherwise identical to that of FIGS. 23 and 24, and will be installed in the same way, and like reference numerals have been used for like parts as appropriate.

Although the mating anti-rotation formations 214, 226 between the two parts of the abutment members in FIGS. 23 to 25 comprise a polygonal post on the first part and a mating bore on the second part, this arrangement may be reversed in alternative embodiments, with the bore at the end of part 202 and a mating, angled post on part 205, 230.

Figures 26, 27:
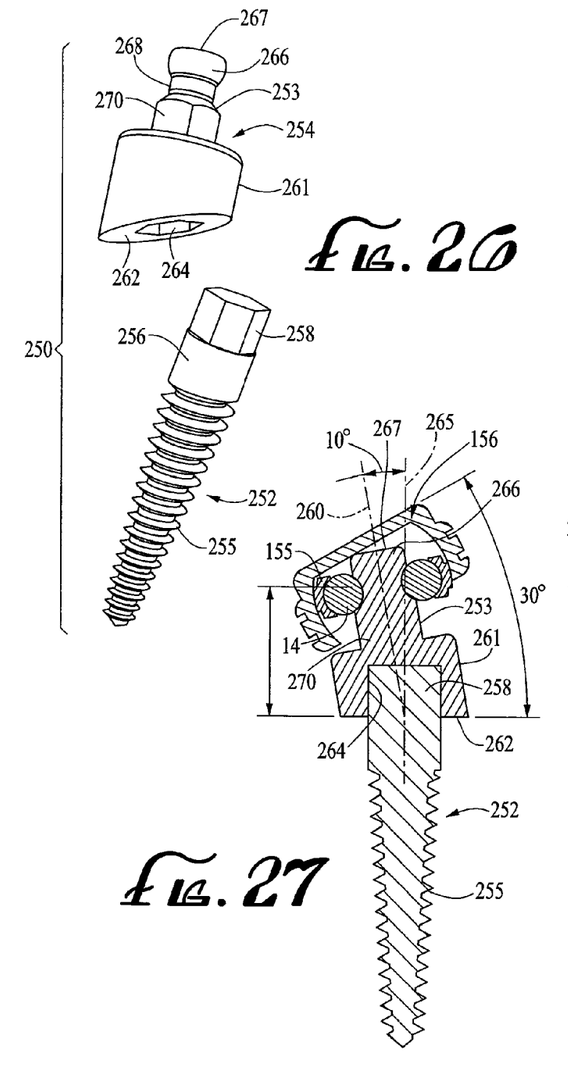
FIG. 26 is a separated perspective view of two parts of an angle correction implant member for an attachment assembly according to another embodiment.
FIG. 27 is a cross-sectional view of an assembled O-ring attachment assembly using the angle correction implant member of FIG. 26.
Figure 28:
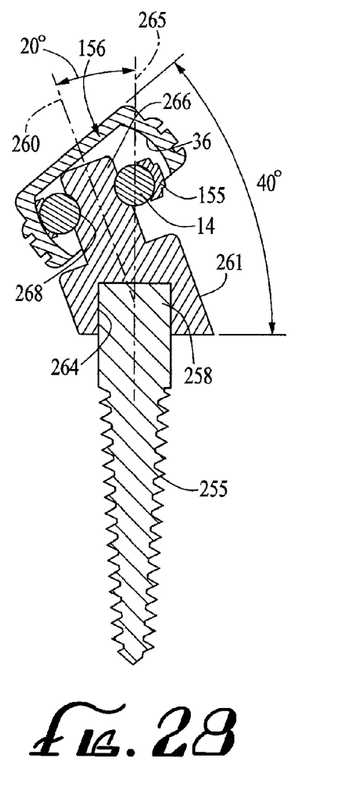
FIG. 28 is a cross-sectional view similar to FIG. 27 illustrating an attachment assembly with a different angular adjustment.

FIGS. 26 to 28 illustrate an attachment assembly with another angled abutment or implant device 250 having a first part 252 and a second, angle-adjusting part 254 for securing to the first part once the appropriate orientation has been determined. The pivoting cap 156, retainer ring 155, and O-ring 14 in this embodiment are identical to that of the previous embodiment, and like reference numbers are used for like parts as appropriate. The first part 252 of the mini-implant device 200 has a tapered, threaded shaft 255 similar to the shaft of mini implant 82 of FIGS. 12 to 14 and of similar dimensions. Shaft 255 is designed for threaded engagement in a prepared bore in endosseous bone, and has an unthreaded portion 256 at its larger diameter end. A hex or other anti-rotation post 258 projects from the unthreaded portion of the shaft.

The first part 252 of the angled abutment or implant 250 is similar to the first part of the abutment device in FIGS. 23 to 25, and has a head portion 253 defining a central axis 260, and an angled portion 261 extending from the head portion having an angled, flat end face 262 which is not perpendicular to axis 260, and a bore 264 in end face 262 having a central axis 265 at an angle to axis 260 and perpendicular to end face 262, as best seen in FIG. 27. Head portion 253 has a rounded head 266 with a flat end 267, an annular groove 268 adjacent the head for receiving an O-ring, and a tool-engaging portion 270 adjacent the groove which may be of hexagonal or other polygonal shapes.

Bore 264 is designed for mating, anti-rotation engagement with the post 258 of the first abutment part 252. In the illustrated embodiment, the bore 264 and post 258 are of mating hexagonal shape, but may be of other polygonal shapes in alternative embodiments. In the embodiment illustrated in FIGS. 26 and 27, the bore 264 extends at an angle of around 10 degrees to the axis 260 of head portion 253 (such that flat end face 262 is at 80 degrees to axis 260), but may be provided at different angles in other embodiments, such as 20 degrees as illustrated in FIG. 28. The attachment assembly in FIG. 28 is otherwise identical to that of FIGS. 26 and 27, and like reference numbers have been used as appropriate.

The angle adjusting part 254 of the implant or abutment device 250 is similar to part 205 of the previous embodiment, except that the tool engaging portion 270 is longer than tool-engaging portion 222, and the angled portion 261 is longer than angled portion 208.

In order to install the attachment assembly, the first part 252 of the mini implant device 250 is first secured in a prepared bore in endosseous bone using threaded shaft 255. A suitable hex tool can engage post 258 in order to install the first part 252 of the abutment. The post 258 will then extend at the same angle as the divergent bore. A second part 254 at an appropriate angle is then selected, based on the angle of the divergent bore and thus the angle of post 258. The second part 254 is rotated until it is at the correct angle to compensate for the angle of post 258, i.e. so that the head portion extends substantially vertically in the jaw, and is then engaged over the post 258 and cemented in place.

The installed abutment device 250 is designed for releasable mating engagement with the same pivoting O-ring or resilient ring in a cap as in the previous embodiments, as indicated in FIGS. 27 and 28. The cap 156, retainer ring 155, and O-ring 14 of this embodiment are the same as in FIGS. 16 to 22, but the device may also be used with the cap, retainer ring, and O-ring of any of FIGS. 1 to 15 in alternative assemblies. The cap 156 containing the pivoting retainer ring 155 and O-ring 14 is first bonded in an indent in a denture or other dental appliance. The O-ring 14 is then snapped over the head 266 of device 250 and engages in groove 268, as illustrated in FIG. 27. The cap 156 can then pivot relative to the head of the abutment or implant device, to provide more compensation for off-angle implants and any deviation of the head portion 253 from the vertical orientation. The angled abutment or implant device 250 of FIG. 26 together with the pivoting cap allow the cap to be pivoted up to 30 degrees relative to the central axis 265 of the threaded mini implant 252 and bore 264 of the first part of the implant device, and thus the axis of the bore in which the implant device is secured.

The attachment assembly of FIG. 28 has a similar two part mini-implant or abutment device to the previous embodiment, except for the fact that the head portion of the abutment device is angled at twenty degrees relative to the axis 265 of the first part 252 and bore 264 on installation, rather than ten degrees as in the previous embodiment, and will be used where a larger correction angle for a divergent implant placement is desired. This assembly allows the cap to be pivoted up to forty degrees relative to the axis 265 of the implant, as indicated in FIG. 28. The assembly of FIG. 28 is otherwise identical to that of FIGS. 26 and 27, and will be installed in the same way, and like reference numerals have been used for like parts as appropriate.

The pivoting O-ring or resilient ring in a cap may be sold separately from the abutment or implant in the above embodiments, and may be provided in various sizes to fit onto existing abutment members with a ball head, if desired. This allows an existing implant or set of implants designed for attachment to an O-ring to be retrofitted with a swiveling cap attachment to allow swiveling as well as vertical motion of an attached denture.

The combination of the vertical movement permitted by the resilience of the O-ring and the swiveling or pivoting motion of the cap over the outer retainer in each of the above embodiments allows for more movement of the denture. The pivoting movement can compensate for off-angle implant placements. Rather than a round ball on the head of the abutment member, a flattened top is provided to reduce the overall height of the abutment.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A dental attachment system, comprising:
    an abutment member configured for attachment to a tooth root, implant, or adjacent tooth, the abutment member having a head and an annular seat adjacent the head, the head having an end face and an outer annular surface extending axially from the end face to the annular seat, and the head and annular seat defining a central longitudinal axis;
    an elastomeric ring configured for releasable engagement in the seat on the abutment member;
    a retainer ring engaged over the elastomeric ring, the retainer ring being of more rigid material than the elastomeric ring, and having opposite open ends and an outer surface which is of rounded, convex cross-sectional shape in the longitudinal direction; and
    a cap for securing in a recess in a dental appliance or prosthesis, the cap having a central longitudinal axis, an inner annular surface which is of rounded, concave cross-sectional shape in the longitudinal direction and which is adapted for swivel engagement over the rounded, convex outer surface of the retainer ring and an inner end face which faces the end face of the head of the abutment member and a first end of the retainer ring, the inner end face of the cap being axially spaced from both the opposing end face of the head and the first end of the retainer ring to define a clearance permitting swiveling of the cap relative to the head and retainer ring through a predetermined angular range from an axially aligned orientation in which the central longitudinal axes of the cap and head are coaxial into swiveled orientations in which the central longitudinal axis of the cap is angled relative to the central longitudinal axis of the head.

2. The assembly of claim 1, wherein the abutment member has a shaft extending co-axially from the annular seat, the shaft having a tail end portion configured for engagement in a mating bore in a non-vital root or in an implant threaded into endosseous bone.

3. The assembly of claim 2, wherein the shaft has a tool-engaging portion of polygonal cross-section adjacent the annular seat.

4. The assembly of claim 3, further comprising an annular flange between the tool-engaging portion and tail end portion.

5. The assembly of claim 2, further comprising threads extending along at least part of the length of the tail end portion.

6. The assembly of claim 2, wherein the abutment member comprises a mini implant and the shaft has a threaded tail portion adapted to be implanted directly into a prepared bore in a patient's jaw.

7. The assembly of claim 6, comprising a plurality of mini implants and a bar extending between the mini implants.

8. The assembly of claim 1, wherein the outer annular face of the head is of rounded, convex shape and the end face of the head is at least substantially flat.

9. The assembly of claim 1, wherein the abutment member has a distal extension configured for securing the abutment member to an adjacent tooth or crown.

10. The assembly of claim 1, further comprising a bar and at least two spaced abutment members secured on the bar, the bar being configured for securing to at least two implants.

11. The assembly of claim 1, wherein the elastomeric ring has an outwardly rounded, convex outer surface and the retainer ring has a concave inner surface configured for mating engagement over the outer surface of the elastomeric ring.

12. The assembly of claim 11, wherein the elastomeric ring is an O-ring of circular cross-section in an axial direction.

13. The assembly of claim 1, wherein the outer surface of the retainer ring has notches adjacent opposite axial ends of the ring.

14. The assembly of claim 1, wherein the abutment member has first part having a shaft configured for engagement in a mating bore in a non-vital root or into an implant threaded into endosseous bone, and a second part extending at an angle to the first part, the head and annular seat being located on the second part of the abutment member, whereby the cap is secured at an angle to the shaft.

15. The assembly of claim 14, wherein the first part is formed separately from the second part, the first and second part having mating, anti-rotation formations configured for engagement of the second part with the first part after installation of the first part in the jaw.

16. The assembly of claim 15, wherein the first part has a head portion comprising the head and annular seat and a second portion having said mating anti-rotation formation, the anti-rotation formation extending at a predetermined angle to the head portion, the anti-rotation formation being aligned with the shaft on engagement with the mating anti-rotation formation on the second part of the abutment member, whereby the head portion extends at said predetermined angle to the shaft.

17. The system of claim 1, wherein the predetermined angular range is at least up to fifteen degrees from the axially aligned orientation.

18. An attachment assembly for releasable snap engagement over the head of an abutment member or implant secured in a patient's mouth, comprising:
    a cap configured for securing in a recess in a dental appliance, the cap having a cavity with an open end facing away from the dental appliance, the cavity being of a first height and having a rounded, concave inner annular surface and a substantially flat inner end face which faces the open end of the cavity;
    a retainer ring engaged in said cavity, the ring having opposite first and second open ends, a rounded, outwardly convex outer surface pivotally engaged with the rounded, concave inner annular surface of said cavity, and a concave inner surface extending between said first and second ends;
    an elastomeric ring retained in said retainer ring and configured for snap engagement over the head of an abutment member or implant secured in a patient's mouth;
    the retainer ring and elastomeric ring together defining a first central longitudinal axis and the cap defining a second central longitudinal axis; and
    the retainer ring having a second height less than the first height, whereby an axial clearance is provided between the first open end of the retainer ring and inner end face of the cavity which allows the cap to swivel relative to the retainer ring and elastomeric ring from an axially aligned orientation in which the first and second central longitudinal axes are coaxial and a predetermined angular range of swiveled orientations in which the second central longitudinal axis is angled out of alignment with the first central longitudinal axis.

19. The assembly of claim 18, wherein the elastomeric ring is an O-ring.

20. A dental attachment system, comprising:

an abutment member configured for attachment to a tooth root, implant, or adjacent tooth, the abutment member having a head and an annular seat adjacent the head, the head having a flat end face and a rounded, convex outer annular surface extending from the flat end face to the annular seat;

an elastomeric ring configured for releasable engagement in the seat on the abutment member;

a retainer ring engaged over the elastomeric ring, the retainer ring being of more rigid material than the elastomeric ring, and having opposite first and second open ends and a rounded, convex outer surface between the ends, the head and annular seat of the abutment member and the rings together defining a first central longitudinal axis; and a cap for securing in a recess in a dental appliance or prosthesis, the cap having a rounded, concave inner annular surface adapted for swivel engagement over the rounded, convex outer surface of the retainer ring and a flat inner end face which faces the flat end face of the head of the abutment member and the first open end of the retainer ring, and defining a second central longitudinal axis, the inner end face of the cap being spaced in the axial direction from both the opposing end face of the head and the opposing first open end of the retainer ring to define an axial clearance permitting swiveling of the cap relative to the head and retainer ring through a predetermined angle from an aligned orientation in which the first and second central longitudinal axes are coaxial and swiveled orientations in which the second central longitudinal axis is angled out of alignment with the first central longitudinal axis; and the flat end face of the head being positioned closer to the flat inner end face of the cap than the first open end of the retainer ring.

21. The system of claim 20, wherein the flat outer end face of the head has a diameter which is greater than the height of the head.

22. The system of claim 20, wherein the rounded outer annular surface of the head is non-spherical.

23. The system of claim 20, wherein the elastomeric ring has a round cross-sectional shape of diameter greater than the height of the head.

24. The system of claim 20, wherein the retainer ring has a height greater than the height of the head.

25. An attachment assembly for releasable snap engagement over the head of an abutment member or implant secured in a patient's mouth, comprising:

an elastomeric ring configured for snap engagement over the head of an abutment member or implant secured in a patient's mouth;

a retainer ring engaged over the elastomeric ring, the retainer ring having a central longitudinal axis and opposite open ends, and having an outer surface and an inner surface which each extend along at least a major portion of the length of the ring between said ends, the outer surface being of convex shape and the inner surface being of concave shape in a direction along the length of the ring;

a cap configured for securing in a recess in a dental appliance and engaged over the retainer ring, the cap having a central longitudinal axis and a cavity with an open end facing away from the dental appliance, the cavity having an inner annular surface which is of concave shape along at least part of the length of the inner annular surface in an axial direction and a substantially flat inner end face which faces the open end of the cavity; and the inner end face of the cap being axially spaced from an opposing open end of the retainer ring and the concave inner surface of the cap being in swivel engagement over the convex outer surface of the retainer ring, the cap swiveling relative to the retainer ring between an aligned orientation in which the central longitudinal axes of the cap and retainer ring are coaxial and offset orientations in which the longitudinal axis of the cap is angled relative to the longitudinal axis of the retainer ring.

* * * * *